United States Patent [19]

Schuss

[11] 4,348,180
[45] Sep. 7, 1982

[54] DEVICE FOR RELEASABLY CONNECTING A HEAD PART TO A HANDLE PART OF A DENTAL HANDPIECE

[75] Inventor: Werner Schuss, Heppenheim, Fed. Rep. of Germany

[73] Assignee: Siemens Aktiengesellschaft, Berlin & Munich, Fed. Rep. of Germany

[21] Appl. No.: 202,136

[22] Filed: Oct. 30, 1980

[30] Foreign Application Priority Data

Nov. 29, 1979 [EP] European Pat. Off. ........ 79104767.3

[51] Int. Cl.³ .............................................. A61C 1/08
[52] U.S. Cl. .................................. 433/126; 403/322; 403/327
[58] Field of Search ................ 433/126; 403/104, 322; 285/319, DIG. 22

[56] References Cited

U.S. PATENT DOCUMENTS 3,229,369  1/1966  Hoffmeister et al. .
4,211,009  7/1980  Leonard ............................... 433/126
4,251,212  2/1981  Worschischek ..................... 433/126

FOREIGN PATENT DOCUMENTS 1107890  5/1961  Fed. Rep. of Germany .
2908390  9/1979  Fed. Rep. of Germany ...... 433/126

Primary Examiner—Robert Peshock
Attorney, Agent, or Firm—Hill, Van Santen, Steadman, Chiara & Simpson

[57] ABSTRACT

A device for releasably interconnecting a head part to a handle part of a dental handpiece characterized by one of the two parts having a catch element in the form of radially projecting catch nose coacting with a counter element in the form of a recess disposed on the other part and a resilient sleeve-shaped member, which forms an outer generated surface of one of said head and handle parts, acting on one of the elements to urge the pair of elements in a coupled state and allowing a disengagement of the elements to enable releasing the connection between the hand parts when a squeezing pressure is applied to the sleeve shaped member.

5 Claims, 8 Drawing Figures

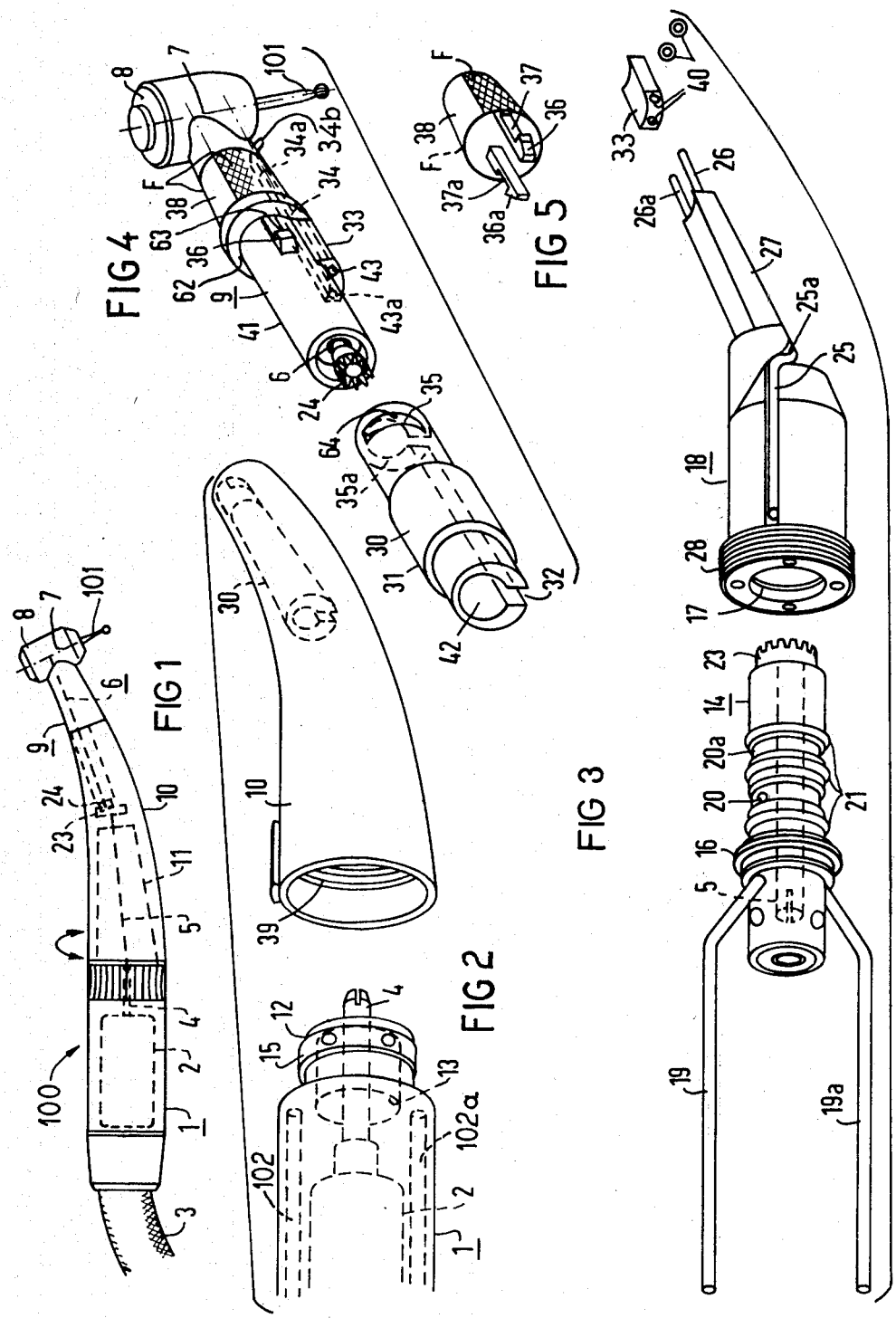

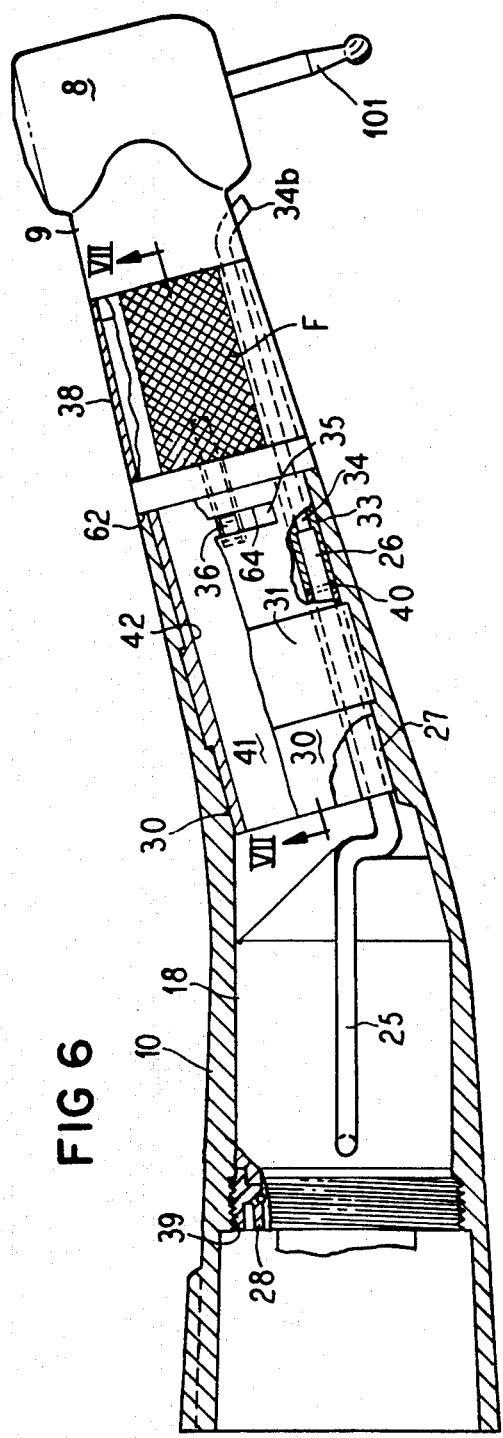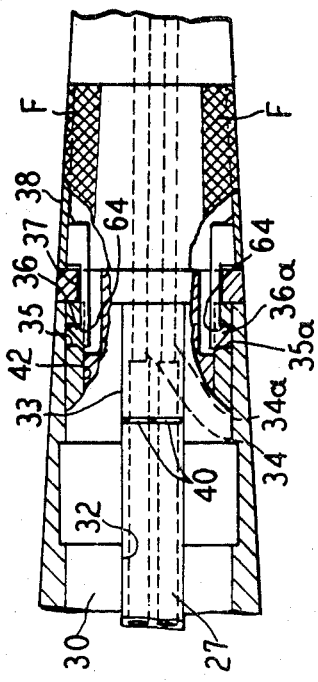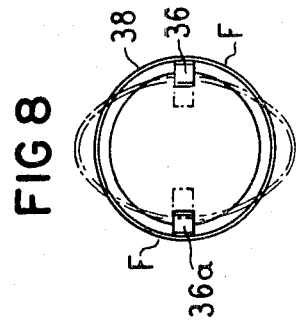

DEVICE FOR RELEASABLY CONNECTING A HEAD PART TO A HANDLE PART OF A DENTAL HANDPIECE

BACKGROUND OF THE INVENTION

The present invention is directed to a device for releasably connecting a head part to a handle part of a dental handpiece.

In the dental practice, the most wide spread type of connection for releasably connecting a head part to a handle part of a dental handpiece is a screwed or threaded connection. However, the threaded connection has a disadvantage of the diameter of the handpiece being increased at the location of the connection. Moreover, such a connection does not allow for a sufficiently quick separation of the connection or coupling and a subsequent recoupling or reconnection of the handpiece parts particularly because of the fine pitched threads which are usually utilized in the threaded connection.

It is further known to connect the head part to the handle part by means of a bayonet joint or catch. However, the twisting of the two handpiece parts with respect to one another which is required by such a joint is not desirable for a dental hand with an angled piece and particularly for a dental handpiece which has cooling agent lines incorporated within the parts or pieces.

To couple dental handpiece parts together, a device is known which contains a radially projecting, spring loaded pin or stop bolt on one of the handpiece parts which engages in a snap ring groove on the other handpiece part when the two handpiece parts are coupled together. To enable uncoupling, an actuation button is provided at another location of the handpiece part and influences the resiliently arranged stop bolt or spring loaded pin and lifts the pin or bolt out of the snap ring groove when the button is actuated. A major disadvantage with such a device is that the actuation button projects beyond the surface of the handpiece.

SUMMARY OF THE INVENTION

The present invention is directed to providing a device for releasably connecting a head part to a handle part of a dental handpiece which device can be easily arranged between the head and handle part without the diameter of the handpiece needing to be noticably enlarged. The device is simple in structure and is easily manipulated when compared to known coupling or connecting devices and in particular contains no projecting actuation parts but nonetheless allows a rapid connection and disconnection of the handpiece parts.

To accomplish these goals, the device for releasably connecting the head part to a handle part comprises at least one catch element coacting with a counter element, and means for biasing the catch and counter elements into engagement, said catch element being a radially projecting catch nose or catch member disposed on one of said parts, said counter element being a recess adapted to receive the catch nose or catch member and being disposed on the other of said two parts, and said means for biasing being a radially resilient sleeve-shaped member acting on one of said elements and forming an outer generated surface for one of said head and handle parts of the dental handpiece so that said sleeve-shaped member urges said elements into a coupled state and a squeezing pressure applied to said member enables disengagement of said elements to release the connection between the head and handle parts.

Preferably, the device includes two catch elements and their corresponding counter elements which are diametrically arranged in the handpiece and preferably the catch elements are supported on the sleeve-shaped member by axially extending bridges or bridge members or elements. The counter elements are preferably grooves formed in a catch sleeve which telescopically receives a neck portion of the head part and the sleeve member is disposed on the neck portion adjacent a head housing thereof. Each of the catch elements is preferably a radially extending catch nose or stop having an engagement surface that coacts with an engagement surface on the slot and the device includes means for biasing the two parts axially away from each other so that the engagement surfaces are in contact with each other. The diametrically arranged catch elements are preferably mounted on the resilient sleeve so that the portion of the sleeve being squeezed to relieve the catch elements is a tangental extension of the head housing.

A significant advantage of the device of the present invention is to be seen by the fact that the sleeve-shaped member which forms the actuation means can be designed with a very thin wall because of the spring properties which it exhibits. Therefore, the diameter of the handpiece part which accepts the sleeve-shaped member can be dimensioned significantly smaller than is possible with the standard threaded connection.

Another advantage is to be seen by the improved manipulation. In contrast to the radially projecting actuation pins or buttons presently used for connecting handpiece parts and which are disruptive in their manipulation, a relatively large surface actuation area now exists which produces hardly any structural alterations and allows a rapid release of the connection by means of simply pressing the sleeve-shaped member. The sleeve-shaped member can be a sleeve with a continuous circumference or on the other hand can also be provided with slots which can receive the catch elements. The catch noses of the catch elements can be radially directed inwardly or towards the outside in the device of the present invention.

The sleeve member for actuating the engagement means can advantageously be arranged directly adjacent the head housing on a so called neck part of the head part and can form at least one part of the outer circumference of the part. The arrangement of the catch and counter elements is thus advantageously undertaken in such a manner that an actuation of the generating surface or sleeve member occurs by pressing the thumb and index finger against the lateral edges of the neck part, i.e. in the areas which are practically tangent to the head housing. A quick and safe connection and disconnection of the parts is thus guaranteed by this manner.

BRIEF DESCRIPTION OF THE DRAWINGS

FIG. 1 is a side view of a dental handpiece in accordance with the present invention;

FIG. 2 is a partial exploded perspective view of the dental handpiece of FIG. 1;

FIG. 3 is a partial exploded perspective of internal parts of the dental handpiece of FIG. 1;

FIG. 4 is another partial exploded view of the head portion and internal parts of the handpiece;

FIG. 5 is a perspective view of a portion of the headpiece illustrated in FIG. 4.

FIG. 6 is a longitudinal cross-sectional view with portions in elevation of the sleeve part and head part assembled together;

FIG. 7 is a partial cross-sectional view with portions in elevation taken generally along line VII—VII in FIG. 6; and FIG. 8 is an end view of the sleeve of FIG. 5 with the released position illustrated in broken lines.

DESCRIPTION OF THE PREFERRED EMBODIMENTS

The principles of the present invention are particularly useful in a dental handpiece generally indicated at 100 in FIG. 1.

The handpiece 100 is composed of a drive section or part 1, an angled portion or part 10 and a head part or portion 9. The drive section or part 1 contains a drive motor 2 for example an electric motor 2, which receives its drive energy by a supply hose 3 and has a drive shaft 4. In the angled portion 10, a drive train composed of drive shafts 5 and 6 transfer rotational motion or output from the drive shaft 4 to a rotatable tool acceptance shaft or socket 7 that receives and supports a dental tool such as a drill 101 for rotation in a head housing 8 of the head part 9. The head housing 8 is part of the head part which accepts the two drive shaft sections 6 and 7 as well as their bearings and which is removably seated on a handpiece gripping sleeve which is an angled portion 10. The sleeve 10 encloses a bearing unit 11 which is formed of two concentric sleeves 14 and 18 (FIG. 3) that have bearing units for the drive shaft section 5 as well as the rotational connection for conveying one or more cooling agents from the drive part or section 1 to the head part or section 9. The handpiece gripping sleeve 10 together with the head part 9 and the bearing unit 11, which will be described in greater detail below, will rotate with respect to the drive part 1 around the longitudinal axis of the handpiece which is the axis of the drive shaft 4.

The drive part 1 (FIG. 2) has a sleeve-like or cylindrical shoulder 12 surrounding a socket 13 indicated in broken lines through which the drive shaft 4 extends. The socket 13 receives one end of the sleeve 14 when the handpiece parts are assembled. On an outer surface of the shoulder or sleeve 12, a ball catch 15 is provided for axially securing the sleeve 14 in the socket 13. The sleeve 14, which is best illustrated in FIG. 3, contains a spring washer 16 which is received in a snap ring groove 17 of the sleeve 18 during assembly and the assembled sleeves 14 and 18 form the bearing unit 11. Two cooling agent lines 19 and 19a are secured to the sleeve 14 and the ends of the cooling lines discharged in a known manner via radial bores or ports into annular channels 20 and 20a, which are sealed from one another by means of packing rings such as O-rings 21. In addition, the sleeve 14 also accepts and supports the first drive shaft 5 which has one end connected to the drive shaft 4 of the motor 2 and the opposite end supporting a bell-shaped drive gear 23 which will be engaged with the gear 24 (FIG. 4) on the drive shaft section 6. In the assembled state, the ends of the cooling lines sections 19 and 19a will project from the sleeve 14 and are engaged in longitudinal grooves and/or bores 102,102a, of a drive housing of the drive part 1 and can be connected to a supply lines which are conveyed in the hose 3.

In an assembled state, sleeve 18 (FIG. 3) is arranged concentric to the sleeve 14 and contains the cooling line sections 25 and 25a which in turn accept the cooling agent from the annular grooves 20 and 20a in a known manner. The cooling lines 25 and 25a terminate in tubular prongs 26 and 26a which are mounted in a diagonally extending portion or extension 27 of the sleeve 18. The sleeve 18 further contains a threaded ring 28, which is rotatably mounted on the sleeve 18 without axial displacement and contains a snap ring groove 18 for engagement with the spring washer 16 when the sleeve 18 is assembled on the sleeve 14. The sleeve 18 is axially secured in the handpiece by means of the threaded ring 28 being threaded into threads 39 (FIG. 2) of the sleeve of the grip portion 10.

The grip portion or part 10 as illustrated in FIG. 2, adjacent the head 9 receives a resilient slotted guide bushing or grasping sleeve 30. As best illustrated in FIG. 4, the bushing 30 has a collar 31 which is snapped into a socket of the grip portion 10. The guide bushing 30 is thus secured in the handpiece portion 10 against axial slippage. As illustrated, the guide bushing 30 is provided with a cylindrical bore 42 and a continuous longitudinal slot 32 which receives the projecting portion 27 of the sleeve 18 and also a longitudinal fitting strip or member 33 of the head part 9. As illustrated, the strip 33 of the head part 9 contains cooling agent line section 34 and 34a which discharge into a common cooling agent discharged nozzle 34b in the area of the tools supported in the head 8.

The guide bushing 30 serves to prevent twisting of the part 18 relative to the part 9 and also contains two circumferentially spaced catch slots 35 and 35a which are shown as being on both sides of the bushing. The slots 35 and 35a receive radial resilient catch noses 36 and 36a when the head part 9 is axially assembled onto the grip section or portion 10. The two catch noses or catch members 36 and 36a are secured on a spring-like tubular sleeve or member 38 (FIG. 5) by means of bridges or bridge members 37 and 37a which extend parallel to the axis of the sleeve. The spring sleeve or resilient member 38 is designed with a very thin wall and is arranged on the head part 9 in such a manner that it forms an outer generated surface. By means of radial pressure against the sleeve 38 for example by using the thumb and index finger, the two catch noses 36 and 36a can be moved radially towards the inside and therefore will be released or disengaged from the slots 35 and 35a.

The bridges 37 need not be absolutely rigidly arranged on the actuation sleeve 38. It is also conceivable within the framework of the invention for the catch nose 36 instead of extending radially outward as illustrated to be arranged to extend radially inward. Variations of the sample embodiment illustrated are also possible with respect to the number of catch noses provided without leaving the framework of the invention. The disposition of the two catch noses lying diametrically opposite one another, however, is particularly advantageous although it is also conceivable to provide only one catch nose or three or respectively four catch noses for specific purposes. An embodiment in which the resilient sleeve is provided with one or more recesses on a circumference and the bridges together with the catch noses are arranged on the member 30 is also within the framework of the present invention.

For assemblying the handpiece, the bushing 30 is first clamped into the grip portion 10. The collar 31 is thus engaged in the corresponding socket of a sleeve-like grip portion 10 and prevents axial dislocation of the bushing. Subsequently, the sleeve 18 is inserted into the handpiece portion 10 with the projection 27 engaged in the longitudinal slot 32 of the guide bushing 30. By means of the threaded ring 28, which is rotatably mounted on the sleeve 18, the sleeve 18 is axially fixed within the handpiece portion 10 as the threads of the ring 28 are received in the internal threads 39.

The sleeve 14 as already mentioned is connected in a twist proof but axially releasable manner on the drive part 1 by means of the ball catch device 15. The handpiece grip or sleeve portion 10 with the guide bushing 30 supported therein and the sleeve 18 with the cooling agent lines 25 and 25a can now be axially slipped onto the sleeve 14 until the spring washer 16 is received by the groove 17 and the two handpiece parts are then axially fixed or connected together.

The head part 9 in addition to including the springlike sleeve 38 has a tubular shank or neck part 41 with a portion of the fitting strip 33 extending from one side thereof. When the head part 9 is assembled with the grip portion 10, the shank 41 is received in the bore 42 of the bushing 30 and the strip 33 is received in a portion of the slot 32. Thus the head part 9 will be secured against twisting relative to the bushing 30 and to the sleeve 18. Prior to assembly, elastic seals 40 consisting of one or more elements are inserted over the prong-like projections 26 and 26a of the coolant lines 25 and 25a. Thus, during assembly the prongs 26 and 26a will be received in sockets 43 and 43a of the member 33 to complete the connection to the cooling agent line sections 34 and 34a. The amount of insertion of the shank into the bore 42 is limited by a shoulder 62 but not until after the catch noses 36 and 36a have ben engaged in the catch slots 35 and 35a so that the head part 9 is first axially fixed with respect to the grip sleeves or portion 10. In the catch position, the seals guarantee a tight connection between the cooling line sections 25 and 34.

In addition, the seals 40 also fulfill another function namely providing sufficient clearance between the two gears 23 and 24 for proper meshing engagement. To this end, the two catch noses 36 and 36a are engaged in the slots 35 and 35a with a slight axial play. The pre-stress force created by the seals 40 will bias the head part 9 away from the grip sleeve 10. Thus, the desired clearance between the handpiece parts in the axial direction is obtained due to the detent of the edge 63 of the catch nose 36 and 36a being engaged tightly against the sides 64 of the slot such as 35 and 35a. Due to this arrangement, the shoulder 62 can be eliminated.

Instead of utilizing the elastic seals 40, a spring wire, a spring band or the like can be inserted at right angles to the cooling fluid line sections 34. These spring members can be provided to act on an end face of the fitting strip or member 33 or a part thereof to urge the head part 9 away from the gripping sleeve 10. This biasing ensures the axially effective pressure and spacing between the two gears 23 and 24 when the handpiece parts are properly connected.

For releasing the head part 9, the spring sleeve 38 is pressed slightly together in a radial direction in the surface areas F which are a knurled outer portion adjacent each of the catch noses 36 and 36a. By means of this pressing together, which is expediently accomplished by the thumb and index finger, the spring sleeve is deformed thereby moving the catch nose from an engagement in the respective slots. The arrangement of the catch connection in the area illustrated allows a safe connection and disconnection of the handpiece parts because the head part need by grasped particularly only at the side surfaces, which is the surface area which merges tangently into the head housing 8.

Although various minor modifications may be suggested by those versed in the art, it should be understood that I wish to embody within the scope of the patent granted hereon, all such modifications as reasonably and properly come within the scope of our contribution to the art.

I claim:

1. A device for releasably connecting a head part having a neck extending from a head housing with a socket for receiving a dental tool to a handle part of a dental handpiece with each part having drive shafts of a drive train extending from the socket in the head housing through the neck and the handle part to a motor in the drive section, said device comprising a radially resilient sleeve-shaped member being disposed on the neck of the head part immediate adjacent to the head housing to form one portion of the outer circumference of the neck of the head part, a pair of catch elements coacting with a pair of counter elements, said sleeve-shaped member acting as means for biasing the catch and counter elements into engagement with each other, each catch element being an outwardly radially projecting catch member disposed on said sleeve-shaped member to be positioned inward of an end of said neck with the catch elements of the pair being diametrically opposite each other, each counter element being a recess adapted to receive the catch member and being disposed on the handle part and aligned with a respective catch element so that said sleeve-shaped member urges said elements into a coupled state and squeezing pressure applied to diametrically opposite portions of said sleeve-shaped member adjacent the catch members enables disengagement of said elements to release the connection between the head and handle parts to enable applying interchangeable head parts on the same handle part.

2. A device according to claim 1, wherein each of said catch elements has an engagement surface and is adapted for insertion into a grasping sleeve arranged in the handle part, said grasping sleeve having said pair of counter elements formed therein as a pair of slots, each slot having an engagement surface for the engagement surface of the respective catch element.

3. A device according to claim 2, which includes biasing means disposed between said head part and handle part for urging the parts axially away from each other to ensure engagement between the engagement surfaces of the slots and catch elements.

4. A device according to claim 1, wherein the sleeve-shaped member merges essentially flush with the remaining adjacent surface of the neck carrying said member.

5. A device according to claim 1, wherein each of said catch elements is formed in an end of a bridge member, said pair of bridge members extending from one end of the sleeve-shaped member and parallel to the axis thereof with the catch elements being shaped from said one end of the sleeve-shaped member.

* * * * *